United States Patent [19]

Isa et al.

[11] 3,952,071

[45] Apr. 20, 1976

[54] METHOD FOR PREPARATION OF OLEFIN OLIGOMER

[75] Inventors: Hiroshi Isa; Toshiyuki Ukigai, both of Yachiyo; Anri Tominaga, Tokyo; Ryozo Taniyasu, Narashino; Masuzo Nagayama, Tokyo, all of Japan

[73] Assignee: Lion Fat & Oil Co., Ltd., Tokyo, Japan

[22] Filed: Jan. 6, 1975

[21] Appl. No.: 538,965

[30] Foreign Application Priority Data

Jan. 29, 1974  Japan.............................. 49-11441

[52] U.S. Cl..................... 260/683.15 B; 260/683.9; 252/429 R
[51] Int. Cl.²........................................... C07C 3/18
[58] Field of Search ............................ 260/683.15 B

[56] References Cited
UNITED STATES PATENTS

| | | |
|---|---|---|
| 2,384,916 | 9/1945 | Holmes..................... 260/683.15 B |
| 2,559,984 | 7/1951 | Montgomery et al...... 260/683.15 B |
| 2,591,384 | 4/1952 | Stevens et al............. 260/683.15 B |
| 2,637,720 | 5/1953 | Schneider et al.......... 260/683.15 B |

Primary Examiner—D. Horwitz
Attorney, Agent, or Firm—Woodhams, Blanchard and Flynn

[57] ABSTRACT

An olefin oligomer having a low viscosity and a high viscosity index can be prepared by polymerizing an olefin having 6 or more carbon atoms in the presence of a mixture of a polyhydric alcohol derivative and an aluminum halide, said derivative being obtained by replacing the hydrogen atoms of all the hydroxyl groups of the polyhydric alcohol by either acyl groups exclusively or by acyl group and alkyl groups both of said groups having 1 - 20 carbon atoms. The thus prepared olefin oligomer scarcely contains halogen, and it has a wide range of uses such as, for instance, a lubricant, a cosmetic base, etc.

6 Claims, No Drawings

METHOD FOR PREPARATION OF OLEFIN OLIGOMER

BACKGROUND OF THE INVENTION

The present invention relates to a novel method for preparation of olefin oligomers and to be precise, it relates to a method for preparation of olefin oligomers which can prevent halogen atoms from being present in the polymerization product and which will provide olefin oligomers having a low viscosity and a high viscosity index.

As a method for polymerization of olefins, the cationic polymerization method employing Lewis acids such as aluminum chloride has been known for a long time. According to this method, however, the degree of polymerization becomes so high under the ordinary reaction conditions that there can be obtained only high-viscosity polyolefin oils. Consequently, a polyolefin oil prepared by the conventional cationic polymerization is in fact disqualified for use as a gas turbine oil, a hydraulic fluid for aircraft, an insulating oil, a cosmetic base and the like. It is admittedly possible to obtain a polyolefin oil having a low viscosity even by the use of aluminum chloride if the reaction temperature is sufficiently high. For instance, a polyolefin oil having a viscosity of 30 centistokes or thereabouts can be obtained by polymerizing octene-1 with aluminum chloride at about 180°C, but in this case, the product polyolefin oil is defective in that not only is the viscosity index thereof as low as 100 – 105 (VIE), but also the halogen of the catalyst is present therein to the extent of several thousand ppm.

The presence of halogen in the polymerization product has a bad influence of grave importance on the process of after-treatment of the polymerization product. For instance, at the time of distilling the unreacted olefin monomer and/or olefin dimer from the polymerization product, there takes place a thermal cracking of a part of the halogen in the polyolefin oil thereby to generate hydrogen chloride, so that the distillation apparatus is corroded thereby. Furthermore, at the time of the hydrogenation of the double bonds remaining in the polymerization product, carried out for the purpose of improving the heat stability as well as the oxidation stability of the polymerization products, there occurs trouble that the Raney nickel used as catalyst for said hydrogenation is rendered inactive by the halogen.

Under these circumstances, there has been proposed the method employing an alkaline aqueous solution or an aqueous ammonia, the method employing an absorbent, etc., for the purpose of decomposing and removing the polymerizaton catalyst prior to subjecting said polymerization product to distillation. All of these methods, however, are defective in that the polyolefin oil obtained thereby contains therein residual halogen to the extent of several thousand or more ppm, so that the cationic polymerizaton method at high temperature employing aluminum chloride has practically been out of use.

There has been proposed in Japanese Pat. Publication No. 3804/1969 a method of effecting polymerization of olefins in the presence of a liquid catalyst prepared by dissolving excess aluminum halide in a complex consisting of aluminum halide and ethyl acetate at the molar ratio of 1:1. However, inasmuch as said complex does not act as a catalyst, the effect of this method is no more than cationic polymerization employing the aluminum halide added in excess. Therefore, even by this method employing a complex, there can be obtained only a polyolefin oil having a high viscosity under the ordinary reaction conditions, like in the case of the foregoing cationic polymerization method. If the reaction temperature is elevated in order to obtain a polyolefin oil having a low viscosity, the viscosity index of the product polyolefin oil will be reduced, causing the same trouble as in the case of the above discussed aluminum chloride catalyst, namely, halogen atoms are present in the product polyolefin oil.

The present invention proposes a novel polymerization method and its object is to prepare an olefin oligomer having a low viscosity and a high viscosity index and which is practically free from halogen atoms therein.

SUMMARY OF THE INVENTION

The method for preparing olefin oligomers according to the present invention comprises polymerizing an olefin having 6 or more carbon atoms in the presence of a mixture consisting of a polyhydric alcohol derivative and an aluminum halide, said derivative being selected from the compounds obtained by replacing the hydrogen atoms of all the hydroxyl groups of the polyhydric alcohol by either acyl group exclusively or by acyl groups and alkyl group.

The starting material olefin for use in the present invention is an $\alpha$-olefin or an internal olefin, and to be concrete monoolefins having 6 or more carbon atoms, such as, hexene-1, octene-1, 2-ethyl ocetene-1, tridecene-3, octadecene-2, etc. are illustrative of the useful olefins. Mixtures of these olefins can be used as the starting olefin.

The polyhydric alcohol derivative used in the present polymerization method is a derivative obtained by replacing the hydrogen atoms of all the hydroxyl groups of the polyhydric alcohol by either acyl group exclusively or by acyl groups and alky groups, wherein both of said acyl groups and alkyl groups have 1 - 20 carbon atoms. The polyhydric alcohol used to obtain these polyhydric alcohol derivatives can be illustrated by ethylene glycol, glycerin, trimethylolpropane, pentaerythritol, 1,2-propanediol, 1,4-butanediol, 1,3-propanediol, diethylene glycol, triethylene glycol, tetraethylene glycol, etc., and the derivatives of such polyhydric alcohols can be illustrated by ethoxyethyl ethoxy ethoxy-ethyl acetate, butoxypropyl acetate, methoxyethoxyethyl propionate, 4-methoxybutyl caproate, lauroxyethyl octanoate, ethylene glycol diacetate, ethylene glycol dicaproate, propylene glycol dipropionate, 1,3-diacetoxypropane, 1,4-diacetoxybutane, trans-1,4-diacetoxybutene, 1,5-diacetoxypentane, diethylene glycol diacetate, dibutylene glycol dipropionate, triethylene glycol didecanoate, and pentaerythritol tetracetate.

Especially, ethoxyethyl acetate, butoxypropyl acetate, ethoxyethoxyethyl acetate, ethylene glycol diacetate, 1,3-diacetoxypropane and 1,4-diacetoxybutane demonstrate a conspicuous effect. In order to obtain a polyolefin oil having an extremely low viscosity such as about 20 centistokes, ethylene glycol diacetate, 1,3-diacetoxypropane and 1,4-diacetoxybutane are most desirable.

In the polymerization method according to the present invention, the amount of said aluminum halide employed is required to be not less than 0.8 mole per 1 ether bond or ester bond of said polyhydric alcohol derivative when the amount of aluminum halide is less than this, smooth progress of the polymerization reaction cannot be expected. On the other hand, the use of aluminum halide in an amount of more than 1.2 mole per one ether bond or ester bond of said polyhydric alcohol derivative, has the disadvantage that there will occur the polymerization due to the catalytic action of the aluminum halide alone, thereby to increase the viscosity of the product polyolefin oil. Therefore, the appropriate mixing ratio of the aluminum halide to the polyhydric alcohol derivative is in the range of 0.8 – 1.0 mole, preferably 0.9 – 1.0 mole, of aluminum halide per 1 ester bond or ether bond of the polyhydric alcohol derivative. The amount of the aluminum halide is in the range of 0.1 – 5 mole.%, preferably 1.0 – 3.0 mole.%, relative to the starting olefin.

The reaction temperature varies with the kind of the polyhydric alcohol derivative as well as aluminum halide employed, but it is generally in the range of 50°– 150°C. In the present method too, the lower the reaction temperature, the higher will be the viscosity of the product, and vice versa. However, when the reaction temperature is too high, the viscosity index of the product polyolefin oil tends to become low, so that it is desirable to adjust the viscosity by selecting the kind of polyhydric alcohol derivative employed. In this connection, when where an ester-type polyhydric alcohol derivative is employed, there is obtained an olefin oligomer manifesting a viscosity of 15 – 30 centistokes at 100°F, whereas when a polyhydric alcohol derivative having both ester bonds and ether bonds is employed, there is obtained an olefin oligomer manifesting a viscosity of 30 – 45 centistokes.

As to the method for effecting the reaction, it is customary to dissolve the aluminum halide in the polyhydric alcohol derivative and then add the starting olefin to the resulting solution thereby to effect polymerization. Although this polymerization is usually effected in the absence of solvent, a solvent may be used for the purpose of facilitating the control of the reaction temperature. The solvent for this purpose can be illustrated by n-pentane, iso-octane, trichloroethane, tetrafluoroethane, etc. The appropriate amount of the solvent for use in this case is in the range of 2¼ times as much as the starting olefin (by volume).

If it is desired to remove the unreacted olefin and/or olefin dimers from the polymerization product obtained by the method of the present invention, this can be achieved by the distillation method or the extraction method. Further, if a hydrogenation treatment is required for the purpose of improving the heat stability and oxidation stability of the oil product, this can be easily effected by the use of a hydrogenation catalyst such as Raney nickel, nickel or kieselguhr, etc.

According to the above described polymerization method, it is possible to obtain a polyolefin oil having a viscosity of as low as 15 – 45 centistokes and a viscosity index (VIE) of as high as 120 – 145, and the product polyolefin oil is practically free of halogen. Said polyolefin oil is of course superior in low-temperature fluidity and oxidation stability and has also has such properties as tastelessness and odorlessness.

If a lubricant base or a cosmetic base is prepared from general olefin polyolefin oils, it is usual to apply such after-treatments as distillation, hydrogenation, etc. subsequent to the polymerization. According to the method of the present invention, however, inasmuch as the product polyolefin oil is free from halogen, during distillation and hydrogenation of the product polyolefin oil, there scarcely occurs corrosion of the distillation apparatus and deactivation of the hydrogenation catalyst. The hydrogenated polyolefin oil of the present invention is low in viscosity and high in viscosity index, is superior in heat stability and oxidation stability, and is tasteless, colorless and odorless, so that it has a wide range of uses as, for instance, a highgrade lubricant like gas turbine oil, a hydraulic fluid for aircraft, a cosmetic base, slipping agent, etc.

As will be understood from the above description, the most characteristic feature of the polymerization method of the present invention resides in the use of a mixture of the above discussed special polyhydric alcohol derivative and aluminum halide as the catalyst, and this mixture causes a very unique effect on the polymerization reaction of the olefin. In other words, a complex of the usual ester, ketone and ether with aluminum halide at the molar ratio of 1:1 is said not to act as a catalyst, and in fact, if there is employed a complex of ethyl acetate or acetone with aluminum halide at the molar ratio of 1:1, the polymerization reaction scarcely progresses as is illustrated by the comparative examples given hereinbelow.

On the contrary, in the case of the use of a mixture of the special polyhydric alcohol derivative and aluminum halide according to the present invention, even when said mixture is a complex wherein 1 mole of aluminum halide is present per 1 ester bond or ether bond, the polymerization of the starting olefin can be easily effected, and in addition, the product polyolefin oil has the advantages that it is low in viscosity and high in viscosity index and is practically free of halogen.

At present, the reaction mechanism of the complex of the polyhydric alcohol derivative with aluminum halide in the olefin polymerization is yet to be clarified. However, it is likely that, as each molecule of said complex has a plurality of ester bonds or ether bonds which are easy to break, a cation is easily produced, and because the molecule of the complex per se is of great bulk, when the polyolefin oil groups attain a fixed molecular weight, the polyolefin oil comes off the complex by virtue of the steric hindrance of the complex, so that the product polyolefin oil has a low viscosity and a high viscosity index. And, it is presumed that, because the halogen in a complex-type catalyst is poor in nucleophilicity, at the time when the polyolefin oil comes off the complex, said polyolefin oil is not accompanied with halogen, so that there is obtained a polyolefin oil scarcely containing halogen.

Hereunder will be given several examples embodying the present invention together with comparative examples.

COMPARATIVE EXAMPLE 1

45.0 g of aluminum chloride were dissolved in 20.0 g of ethyl acetate by the use of a 1 $l$ glass autoclave with stirrer (molar ratio of ethyl acetate to aluminum chloride = 1:1.5). Subsequently, 600 g of octene-1 was added dropwise into said autoclave at 140°C for 3 hours. After the addition, aging was effected for 1 hour, ammonia gas was then blown into the autoclave, and the separated catalyst was removed by filtration. Thereafter, the polymerization product was subjected to distillation so as to remove the unreacted olefin and olefin dimer, whereby a product polyolefin oil was obtained. The yield of this polyolefin oil was 82%, and the viscosity of said oil at 100°F was 70 centistokes and the viscosity index thereof was 101. The chlorine content in the polyolefin oil was 2,500 ppm.

Further, when the polyolefin oil was subjected to hydrogenation with Raney nickel catalyst, said Raney nickel became inactive and there was obtained a hydrogenated oil having a bromine number of 9.0.

COMPARATIVE EXAMPLE 2

After dissolving 14.3 g of aluminum chloride in 6.2 g of acetone by the use of the same autoclave as in Comparative Example 1 (molar ratio of acetone to aluminum chloride = 1:1), polymerization was attempted by slowly adding 600 g of octene-1 into said autoclave, but there was observed little progress of the reaction.

EXAMPLE 1

After putting a prescribed amount of polyhydric alcohol derivative and 14.3 g of aluminum chloride in a 1 l glass autoclave with stirring and elevating the temperature up to 100°C, polymerization was effected for 5 hours by slowly adding 600 g of octene-1 into said autoclave. After completing the reaction, ammonia gas was blown into the polymerization product to inactivate the catalyst and the thus separated catalyst was removed by filtration. Thereafter, the polymerization product was subjected to distillation thereby to remove the unreacted olefin and olefin dimer therefrom.

The resulting polyolefin oil was subjected to 3 hours' hydrogenation at a temperature of 150°C and under a hydrogen pressure of 8 Kg/cm² in the presence of 20 g of Raney nickel, whereby a hydrogenated oil was obtained.

The following Table -1 shows the kind of polyhydric alcohol derivative applied, the amount of aluminum chloride employed (in terms of the number of moles of AlCl₃ per 1 ether bond or ester bond of polyhydric alcohol derivative), the yield of the polyolefin oil, the kinematic viscosity of the hydrogenated oil at 100°F, the viscosity index (VIE) and the bromine number, respectively.

In the case of each experiment in the present example except for Experiment No. 2 and No. 3 (comparative examples), there was observed no corrosion of the distillation apparatus nor inactivation of the hydrogenation catalyst, and it was possible to reuse the hydrogenation catalyst. In the case of Experiment No. 3, inactivation of the hydrogenation catalyst was observed.

EXAMPLE 2

After putting a prescribed amount of the respective polyhydric alcohol derivatives shown in the following Table 2 and 14.3 g of aluminum chloride in the same autoclave as employed in Example 1 and elevating the temperature up to 120°– 130°C, polymerization was effected for 5 hours by slowly adding 600 g of octene-1 into said autoclave. After completing the reaction, ammonia gas was blown into the polymerization product to inactivate the catalyst and the thus separated catalyst was removed by filtration. Thereafter, the polymerization product was subjected to distillation to remove the unreacted olefin and olefin dimer therefrom, whereby there was obtained a polyolefin oil. Subsequently, by subjecting this polyolefin oil to hydrogenation under the same conditions as in Example 1, there was obtained a hydrogenated oil. When the kinematic viscosity, viscosity index (VIE) and bromine number of this hydrogenated oil at 100°F were measured, the results were as shown in Table -2.

In this connection, the amount of the polyhydric alcohol derivative for use in each experiment except for Experiment No. 7 was so adjusted as to make the amount of aluminum chloride be 1.0 mole per 1 ester bond or ether bond of said derivative.

Table-2

| | | | Reaction temperature : 120–130°C | | |
|---|---|---|---|---|---|
| Experiment No. | Polyhydric alcohol derivative | Yield of polyolefin oil(%) | Viscosity (centistoke) | Viscosity index (VIE) | Bromine number |
| 6 | ethylene glycol diacetate (7.8 g) | 85 | 21.5 | 128 | 0.2 |
| 7 | The same as above | 75 | 20.5 | 128 | 0.2 |
| 8 | 1,3-diacetoxypropane (8.6 g) | 75 | 18.5 | 128 | 0.2 |
| 9 | 1,4-diacetoxybutane (9.3 g) | 74 | 22.3 | 130 | 0.3 |

(Remark)
The amount of aluminum chloride employed in Experiment No. 7 was 0.9 mole per 1 ester bond of ethylene glycol diacetate.

In the case of each experiment in the present example, generation of hydrogen chloride was not observed at the time of distillation of the polymerization product nor was there observed any inactivation of the catalyst at the time of the hydrogenation treatment of the polyolefin oil. In this connection, when the Raney nickel recovered after the hydrogenation treatment in each experiment was reused as the catalyst for hydrogena- Table-1

| Experiment No. | Polyhydric alcohol derivative | AlCl₃ (molar ratio) | Yield of polyolefin oil (%) | Viscosity (centistoke) | Viscosity index (VIE) | Bromine number |
|---|---|---|---|---|---|---|
| 1 | 2-ethoxyethyl acetate (7.1 g) | 1.0 | 85 | 40.1 | 132 | 0.3 |
| 2 | The same as above | 0.7 | (no reaction) | | | |
| 3 | The same as above | 1.5 | 84 | 75 | 108 | 6.5 |
| 4 | butoxypropyl acetate (11.3 g) | 1.0 | 82 | 38.2 | 130 | 0.3 |
| 5 | ethoxyethoxyethyl acetate (9.4 g) | 1.0 | 85 | 39.5 | 128 | 0.3 | tion of the polyolefin oil, each Raney nickel proved capable of producing hydrogenated oil with a bromine number of 0.2 – 0.5.

EXAMPLE 3

When octene-1 was polymerized under the same conditions as in the foregoing Experiment No. 1 except for elevating the reaction temperature from 100°C to 150°C, and then the resulting polyolefin oil was hydrogenated, the yield of the polyolefin oil was 75%, and the hydrogenated oil displayed a kinematic viscosity of 22.0 centistokes at 100°F, a viscosity index (VIE) of 120 and a bromine number of 0.2. And, even in the present example, generation of hydrogen chloride was not observed at the time of distillation of the polymerized product, and it was possible to reuse the catalyst recovered after the hydrogenation treatment.

EXAMPLE 4

When the polymerization reaction was effected under the same conditions as in Experiment No. 6 except for replacing octene-1 with dodecene-1 as the starting olefin and increasing the amount of said starting olefin up to 700 g, and then the resulting polyolefin oil was hydrogenated, the yield of the polyolefin oil was 85%, and the hydrogenated oil displayed a kinematic viscosity of 35 centistokes at 100°F, a viscosity index (VIE) of 145 and a bromine number of 0.3. And, even in the present example, generation of hydrogen chloride was not observed at the time of distillation of the polymerization product, and the catalyst recovered after the hydrogenation treatment could be reused.

What is claimed is:

1. A method of preparing an olefin oligomer, which comprises polymerizing at a temperaure of from 50° to 150°C, a monoolefin or a mixture of monoolefins having 6 or more carbon atoms, in the presence of a catalyst mixture of aluminum chloride and a polyhydric alcohol derivative selected from the group consisting of ethoxyethyl acetate, butoxypropyl acetate, ethoxyethoxyethyl acetate, methoxyethoxyethyl propionate, 4-methoxybutyl caproate, lauroxyethyl octanoate, ethylene glycol diacetate, ethylene glycol dicaproate, propylene glycol dipropionate, 1,3-diacetoxypropane, 1,4-diacetoxybutane, trans-1,4-diacetoxybutene, 1,5-diacetoxypentane, diethylene glycol diacetate, dibutylene glycol dipropionate, triethylene glycol didecanoate, and pentaerythritol tetracetate, the amount of said aluminum chloride being in the range of from 0.1 to 5 mole %, based on said olefin, and the molar ratio of said aluminum chloride to said derivative being from 0.8 to 1.0 mole of aluminum chloride per one ether bond or ester bond of said derivative, and recovering an olefin oligomer from the polymerization reaction mixture.

2. A method according to claim 1, wherein the amount of aluminum chloride contained in said catalyst mixture is in the range of 0.9–1.0 mole of aluminum chloride per 1 ether bond or ester bond of said polyhydric alcohol derivative and in the range of 1.0–3.0 mol %, based on said olefin.

3. A method according to claim 1, wherein said polymerization is effected in a solvent selected from the group consisting of n-pentane, iso-octane, trichloroethane and tetrafluoroethane in an amount of 25 – 200% by volume, based on the olefin.

4. A method according to claim 1, wherein said polyhydric alcohol derivative is selected from the group consisting of ethoxyethyl acetate, butoxypropyl acetate, ethoxyethoxyethyl acetate, ethylene glycol diacetate, 1,3-diacetoxypropane and 1,4-diacetoxybutane.

5. A method according to claim 1, wherein said polyhydric alcohol derivative is selected from the group consisting of ethylene glycol diacetate, 1,3-diacetoxypropane and 1,4-diacetoxybutane.

6. A method according to claim 1 in which said aluminum chloride is dissolved in said polyhydric alcohol derivative and then said olefin is added to the catalyst solution.

* * * * *